United States Patent [19]

Minnich

[11] Patent Number: 5,308,919
[45] Date of Patent: May 3, 1994

[54] METHOD AND APPARATUS FOR MONITORING THE ARTERIOVENOUS OXYGEN DIFFERENCE FROM THE OCULAR FUNDUS

[76] Inventor: Thomas E. Minnich, 828 Summerhill Dr., Friendsville, Blount County, Tenn. 37737

[21] Appl. No.: 874,022

[22] Filed: Apr. 27, 1992

[51] Int. Cl.$^5$ .............................................. A61B 5/00
[52] U.S. Cl. .................................... 128/633; 128/666; 128/691; 356/41; 351/221
[58] Field of Search ................. 128/633, 664, 665–666, 128/676, 691; 356/41, 319, 320; 351/205.6, 221

[56] References Cited

U.S. PATENT DOCUMENTS

| | | |
|---|---|---|
| 3,847,483 | 11/1974 | Shaw et al. |
| 4,114,604 | 9/1978 | Shaw et al. |
| 4,166,695 | 9/1979 | Hill et al. |
| 4,253,744 | 3/1981 | Sawa |
| 4,350,163 | 9/1982 | Ford et al. |
| 4,579,430 | 4/1986 | Bille |
| 4,694,833 | 9/1987 | Hamaguri |
| 4,697,593 | 10/1987 | Evans et al. |
| 4,824,242 | 4/1989 | Frick et al. |
| 4,836,207 | 6/1989 | Bursell et al. |
| 4,838,683 | 6/1989 | Ichihashi et al. |
| 4,907,876 | 3/1990 | Suzuki et al. |
| 4,941,741 | 7/1990 | Mizuta |
| 5,119,814 | 6/1992 | Minnich ........................... 128/633 |

OTHER PUBLICATIONS

Compilation of papers presented at the Elev. Ann. Scientific and Educ. Symposium of the Soc. of Critical Care Med. in St. Louis MO, Jun. 4, 1982.
Sensitive and Inexpens. Dual-Wavelength Reflection Spectophotometry Using Interference Filters, Duckrow, La Manna, and Rosenthall. In: Reflectance Spectrophotometry, pp. 13–23.

Primary Examiner—Angela D. Sykes
Attorney, Agent, or Firm—Pitts & Brittian

[57] ABSTRACT

A non-invasive eye oximeter which monitors the arteriovenous oxygen difference. The optic disc region of the ocular fundus is illuminated with three or more wavelengths of light focused in approximately the same area. One of the light sources serves as a tracking beam which, through reflectance spectrophotometry, is used to determine when the tracking light beam is focused upon the optic disc. The scanning light beams are primarily focused within the boundary of the tracking beam. The intensity of light reflected from retinal venules and arterioles is detected, and the arteriovenous oxygen difference is determined.

16 Claims, 4 Drawing Sheets

METHOD AND APPARATUS FOR MONITORING THE ARTERIOVENOUS OXYGEN DIFFERENCE FROM THE OCULAR FUNDUS

This application in part discloses and claims subject matter disclosed in our earlier filed pending application, Ser. No. 07/558,082 which was filed on Jul. 25, 1990; now U.S. Pat. No. 5,119,814.

TECHNICAL FIELD

The present invention relates to the medical practice of monitoring arteriovenous oxygen difference. Specifically, the invention relates to an apparatus and method for non-invasively measuring this physiologic parameter by reflectance spectrophotometry.

BACKGROUND ART

It is necessary to determine arteriovenous oxygen difference, or a-v$O_2$ in order to determine cardiac output, which is an important physiologic parameter, during surgical procedures, post-operative monitoring and the management of critically ill patients. Cardiac output, or C.O. is equal to oxygen consumption, $\overline{V}O_2$, divided by arteriovenous oxygen difference, a-v$O_2$. The relationship can be stated algebraically as:

$$C.O. = \frac{\overline{V}O_2}{a-vO_2}$$

While there are non-invasive methods for determining oxygen consumption, $\overline{V}O_2$, at the present time, there are only invasive methods for determining arteriovenous oxygen difference, a-v$O_2$. The non-invasive method for determining arteriovenous oxygen difference of the present method would thus allow cardiac output to be determined without the need for invasive procedures with the attendant risks of infection, bleeding and other trauma. The present invention utilizes the optic disc as the monitoring site. This site was chosen because it has the most accessible peripheral arterioles and venules for non-invasive monitoring.

Prior art using the eye to measure oxygen saturation focused on different portions of the fundus. In U.S. Pat. No. 4,485,820, Flower disclosed a scleral contact lens with a fiberoptic apparatus which measured the hemoglobin saturation of the choroidal arteries. This corresponded to the arterial saturation in, primarily, premature infants. Rather than focusing on the optic disc, Flower utilized the capacity of the eye to serve as an integrating sphere, thereby providing the largest possible surface area to monitor choroidal (arterial) oxygen saturation. Also, Flower did not determine venous oxygen saturation and, therefore, did not determine arteriovenous oxygen difference.

In U.S. Pat. No. 4,877,322, Hill described the use of a collimated beam of light to view specific areas of the fundus, such as the macula, or the optic disc. The ratio of oxyhemoglobin to reduced hemoglobin of these particular areas allows the physician to detect macular degeneration or glaucoma at its early stages.

Novack, in U.S. Pat. No. 4,922,919, measures the oxidative metabolism in ocular tissue by taking advantage of the absorption peak of cytochrome c oxidase. Novack primarily employs an optical probe, which penetrates the ocular body. While Novack describes an alternative apparatus which consists of a contact lens, and subsequently mentions that the invention can also measure desaturated hemoglobin, arteriovenous oxygen difference is not determined. Additionally, Novack does not specifically target the optic disc.

In "The Choroidal Eye Oximeter: An Instrument for Measuring Oxygen Saturation of Choroidal Blood in vivo," *IEEE Trans. Biomedical Engineering*, Vol. BME-22, No. 3, pp. 183-193, 1975, Laing, R. A., et al., the authors make no distinction between the oxygen saturation of choroidal venous and arterial blood.

As mentioned above, arteriovenous oxygen difference, is a highly useful physiologic parameter. Shepherd et al. designed a spectrophotometer which could analyze the arteriovenous oxygen difference, when venous and arterial blood were pumped from dogs into cuvettes. See, Shepherd, A. P. and C. G. Burgar, "A solid-State Arteriovenous Oxygen Difference Analyzer for Flowing Whole Blood," *Amer. J. Physiol.*, Vol. 232, pp. H437–H440, 1977. More recently, Suga et al. devised an instrument which measures not only arteriovenous oxygen content difference, but arterial and venous oxyhemoglobin saturation as well. See, Suga, Hiroyuki, et al., "Arteriovenous Oximeter for $O_2$ Content Difference, $O_2$ Saturation and Hemoglobin Content", *Amer. J. Physiol.* 257 (Heart Circ. Physiol. 26): pp. H1712–H1716, 1989. This is an invasive technique that requires cannulation of the subject's artery and vein.

In U.S. Pat. No. 4,305,398, Sawa discloses an eye oximeter for measuring the oxygen saturation of the blood in the fundus of the eye. Sawa recognized that the problem with this type of analysis is the difficulty in discriminating the reflection or absorption of light by the eye fundus blood from the reflection or absorption of light by the various cell layers in the eye fundus. Sawa's approach to solving this problem utilized the phenomenon in which visual pigments in photoreceptor cells may become transparent upon being illuminated by light.

In U.S. Pat. No. 3,565,529, Guyton, discloses a device for providing continuous measurement of the difference between the amount of oxygen in arterial and venous blood. Guyton disclosed an analyzer which determines the oxygen difference in arterial and venous blood. Light of a narrow wavelength is passed through venous blood and arterial blood that has been pumped into cuvettes. This required catheterization of an artery and a vein in order to pump blood through the cuvette and back into the subject's blood stream.

It is known that when red-free light (e.g. green) is shone into the optic fundus, the optic disc, which is free of photoreceptors, appears brighter than the surrounding fundus background. In fact, with the appropriate wavelength of green light, the retinal vasculature appears almost black. See, Paton, D., et al., In: *Introduction to Ophthalmoscopy*, Edited by B. A. Thomas, Kalamazoo, Mich.: Upjohn Company, 1979, p. 10. Additionally, the maximum absorption wavelength for mammalian rods is 500 nm, and for cones is 562 nm. See, Sharkov, A. V. and Yu A. Matveets, "Ultrafast Processes to Rhodopsins", In: *Laser Picosecond Spectroscopy and Photochemistry of Biomolecules*, 1987, p. 58.

It has been demonstrated that determination of oxyhemoglobin saturation values can be achieved in vessels as small as 12 microns diameter, using reflectance spectrophotometry. See, Fenton, B. M., et al., "Determination of Microvascular Hemoglobin saturations using Cryospectrophotometry," *Amer. J. Physio.* 259 (Heart Circ. Physiol. 28): pp. H1912-H1920, 1990. Also, Fenton states that the hematocrit for microvasculature tends to vary from one vessel to another. However, the arteriovenous oxygen difference is independent of hematocrit, at least up to a hematocrit value of 60 to 70%. See, Steinke, J. M., et al., "Role of Light Scattering in Spectrophotometric Measurements of Arteriovenous Oxygen Difference," *IEEE TRANS. BIOMEDICAL ENGINEERING*, Vol. BME-33, No. 8, pp. 729-734, 1986.

Accordingly, it is an object of the present invention to provide a method and apparatus which can detect arterial and venous oxyhemoglobin saturation in vivo, non-invasively, and atraumatically.

It is another object of the present invention to consistently determine and distinguish between venous and arterial oxyhemoglobin saturation by scanning the optic disc, thereby allowing a determination of the arteriovenous oxygen difference.

It is yet a further object of the present invention to provide a method and apparatus for scanning the optic disc region of the fundus in a linear or curvilinear pattern, thus allowing more than one venule and arteriole pair to be analyzed.

Still another object of the present invention is to provide an apparatus with the capability of sensing the optic disc region of the fundus and accordingly monitoring the optic disc when the optic disc is targeted by the scanning light sources, thus reducing the inaccuracy that results from head and eye movement and that also results from absorbance and reflectance of light by the surrounding fundus tissue layers.

Still yet another object of the present invention is to provide a method and apparatus for determining the arteriovenous oxygen difference in a given patient over a period of time and series of readings thus allowing the patient in question to provide his or her own base line reference.

It is yet another object of the present invention to provide an apparatus for non-invasively determining arteriovenous oxygen difference that is sufficiently mobile to allow examination of multiple patients in separate rooms or facilities.

Other objects and advantages over the prior art will become apparent to those skilled in the art upon reading the detailed description together with the drawings as described as follows.

DISCLOSURE OF THE INVENTION

The present invention pertains to an optic disc scanner and a non-invasive method for using the optic disc scanner for determining the arteriovenous oxygen difference in the eye. The optic disc region of the ocular fundus was selected as the scanning site for two reasons. First, the fundus is the most readily accessible region of the body for non-invasive vascular studies. Second, the optic disc consistently provides both arterioles and venules in close proximity in animal as well as human subjects. This proximity of vessels allows both arteriolar and venular oxygen saturation to be detected virtually simultaneously without the interference caused by the surrounding fundus tissue layers.

The present method employs a novel way of locating the optic nerve head. Since the retina contains more rods than cones, a tracking beam having a wavelength of approximately 520 nm is utilized. At such a wavelength, reflected signals from vessels and retinal photoreceptors is minimized and reflectance is maximized when this wavelength of light strikes the optic nerve head. The apparatus is constructed such that the scanning beams are focused on a spot within the diameter of the tracking beam point of focus.

In the preferred embodiment, the reflected tracking beam signal, i.e. the image of the surface of the fundus, would be focused on a photodetector which would convert the reflected light into an electrical impulse. A signal processing system would detect an increased reflectance as the tracking beam struck the optic disc and signal the light source control to initiate the scanning sequence. The tracking beam is deactivated by the light source control at the same time that the scanning beams are activated. The scanning beams are activated in a rapid, pulsatile and alternating manner. The scanning sequence lasts for approximately 1/10th of a second. Thus, by employing reflectance spectrophotometry, a tracking beam of the correct wavelength allows the device to distinguish the optic nerve head from the surrounding retina thereby allowing preferred scanning of the arterioles and venules associated with the optic disc.

In an alternate embodiment, an operator would visually see when the tracking beam is focused on the optic nerve head. The operator would then trigger a scanning sequence that would last approximately 1/10th of a second. As in the preferred embodiment, the tracking beam is deactivated by the light source control at the same time that the scanning beams are activated.

The vessels of interest are the retinal arterioles and venules, where they emerge from and overlie the optic disc. In this region, vessel diameter ranges from 100 to 140 microns. Furthermore, as the same fundus region of vasculature is scanned each time, the variability of hematocrit becomes inconsequential at this level.

The optic disc scanner would use a specific set of wavelengths for determining arteriovenous oxygen difference. However, an alternate embodiment could have scanning beams of a different wavelength and would be used to determine the saturation level of carbon monoxide saturation in the hemoglobin and thus monitor the progress of treatment in an instance of carbon monoxide poisoning.

BEST MODE FOR CARRYING OUT THE INVENTION

Figure 1:
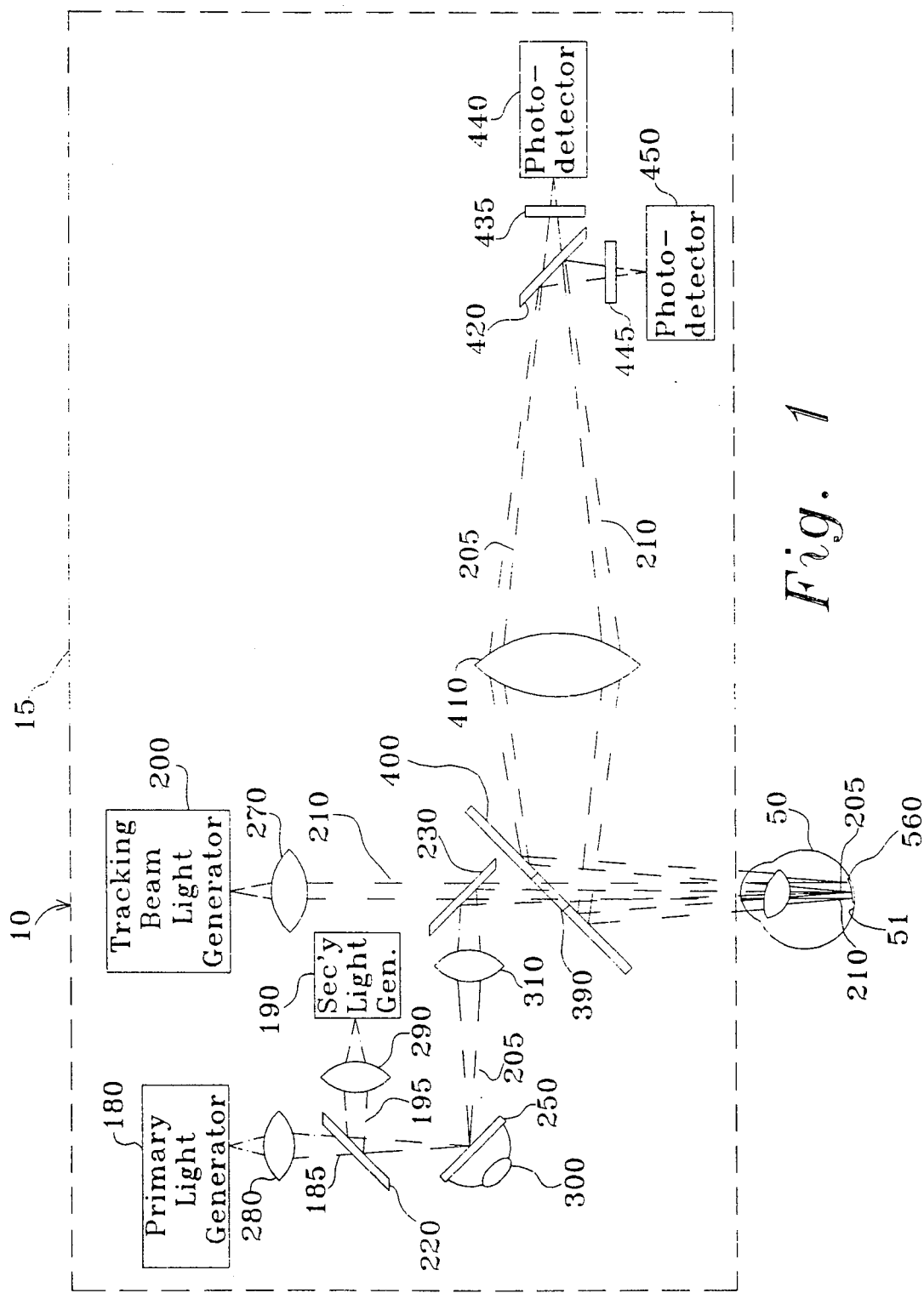
FIG. 1 is a schematic block diagram of an embodiment of the optical system used for focusing the tracking light beam and the primary and secondary light beams of the present invention.

An apparatus for scanning the optic disc region of the ocular fundus for determining arteriovenous oxygen difference non-invasively is illustrated generally as 10 in the figures. In FIG. 1, a schematic block diagram of the preferred optical system 15 above the cornea is shown. Tracking beam light generator 200, which consists preferably of a light emitting diode (LED), emits tracking beam 210. Tracking beam 210 is free of red light, i.e. has a wavelength of 589 nm (yellow) or shorter, the preferred light for the tracking beam 210 has a wavelength of 520 nm. It will be recognized by those skilled in the art that either a laser diode which emits at this frequency or a polychromatic light source in conjunction with a spectral isolator, such as a narrow bandpass filter, that would transmit light of this frequency could also be utilized.

Tracking beam 210 is collimated by collimating lens 270 and then passes through beam splitter 230. Tracking beam 210 passes through aperture 390 in mirror 400 and then enters the eye 50 and forms a spot of illumination having a diameter in the range of approximately 2000 to 2400 microns on the fundus 51. The tracking beam spot of illumination is large enough to envelope the entire optic disc 560. As tracking beam 210 is reflected from the fundus of eye 50, it strikes mirror 400 and is focused by focusing system 410. Tracking beam 210 then is diverted by beam splitter 420 to photodetector 450. Photodetector 450 is a narrow bandwidth photodetector that complements the wavelength of the tracking beam, preferably able to detect in the 500-540 nm range. Alternately, spectral isolator 445, which preferably is a narrow band pass filter in the 520 nm range, could be used so as to allow only light of the frequency of the tracking light beam to be detected by photodetector 450. The signal from photodetector 450 is then transmitted to signal processing means 700, in FIG. 4.

As an alert subject's eyes move, tracking beam 210 will "locate" optic disc 560. In green light, the optic disc 560 reflects a higher intensity signal than the surrounding fundus. When this higher intensity signal is detected by second photodetector 450, signal processing means 700 in FIG. 4, by means of a feedback control loop between signal processing means 700 and light source control means 600, activates the primary and secondary light generators 180 and 190, respectively. As light source control 600 activates the primary and secondary light generators 180 and 190, the tracking beam light generator 200 is simultaneously deactivated by light source control 600. Light source control 600 activates primary and secondary light generators 180 and 190 in a rapid, pulsatile and alternating manner. Minimal eye movement occurs during the scanning interval which is in the range of approximately 10 milliseconds to 1/10th second scan time.

During the aforementioned scan time, a primary light generator 180 emits a primary light beam 185 which has a wavelength of light that has a low absorbance by oxyhemoglobin, preferably in the range of approximately 670 nm. A secondary light generator 190 emits secondary light beam 195. Secondary light beam 195 is of an isobestic wavelength, such as 803 nm. By using light of an isobestic wavelength, reflectance is independent of oxygen saturation and thus the secondary light beam serves as a reference signal. Primary beam 185 and secondary beam 195 are focused through primary beam lens 280 and secondary beam lens 290 respectively.

Primary light beam 185 and secondary light beam 195 strike beam splitter 220. Beam splitter 220 is positioned such that primary light beam 185 and secondary light beam 195 are focused as conjoined light beam 205 on mirror 250, Which is attached to actuator 300.

In the preferred embodiment, actuator 300 consists of a galvanometer. Actuator 300 imparts a slight oscillation to mirror 250 about either its longitudinal or latitudinal axis thereby causing conjoined light beam 205 to inscribe a small linear path of light onto the optic nerve head. In an alternate embodiment, actuator 300 can consist of piezoelectric components. By this means, it will be recognized that a slight amount of oscillation about both the longitudinal and latitudinal axis of mirror 250 would result in a curvilinear path of light being transcribed by conjoined light beam 205 onto the optic nerve head.

Figure 2:
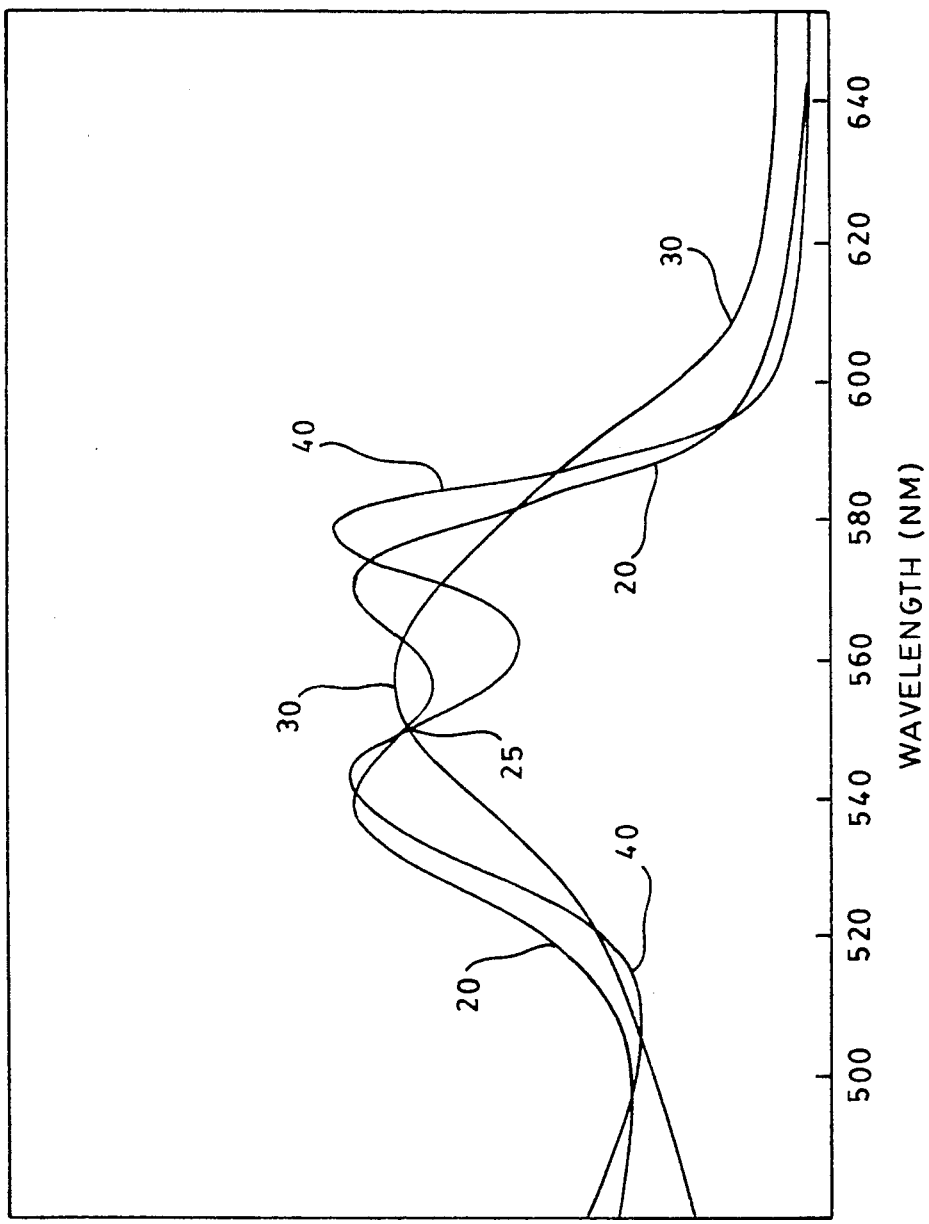
FIG. 2 is an illustration of the absorption spectra of oxyhemoglobin, deoxyhemoglobin and carboxyhemoglobin.

As conjoined light beam 205 is reflected from first mirror 250, conjoined light beam 205 is focused by focusing system 310. From there, conjoined light beam 205 strikes beam splitter 230. Beam splitter 230 reflects conjoined light beam 205 through aperture 390 in mirror 400 and conjoined light beam 205 then enters the cornea of eye 50. The combined focusing power of the foregoing lenses as well as the subject's own eye result in the conjoined primary and secondary light beams having a diameter of 50 to 100 microns each as they impinge on the optic disc 560 vasculature. This diameter is calculated to be less than the diameter of the arterioles and venules of this region, FIG. 2. The timing of the alternating pulses is such that a pulse from primary light beam 185 and a pulse from secondary light beam 195 will each strike the same venule or arteriole. As the beams are moved by the action of actuator 300, a new arteriole or venule will be scanned by a pulse from each of the light beams. The maximum length of this scan pattern is small enough to be contained within the border of the optic disc 560.

It will be recognized by those skilled in the art, that while a particular light path has been described, the invention should not be limited to this particular light path. This is the preferred optical system for focusing the scanning beams within the focus spot of the tracking beam. Those skilled in the art will recognize that alternate light paths could be constructed such that the scanning beams would be focused within the focus spot of the tracking beam and are thus within the scope of the present invention.

Figure 3:
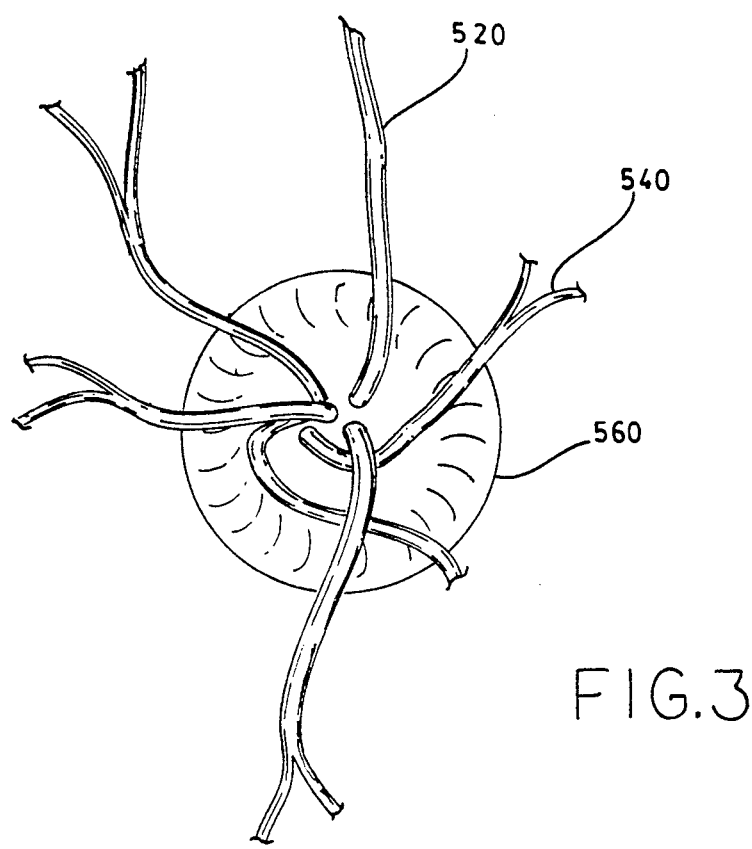
FIG. 3 is an illustration of the optic disc region of interest of the ocular fundus.

Back-scattered light from the hemoglobin in the illuminated venules 520 and arterioles 540, as well as the optic disc 560 itself, FIG. 3, is reflected back through cornea of eye 50, FIG. 1, striking mirror 400. Mirror 400 is oriented in a 45° angle to a line perpendicular to the optic disc 560 rather than the optical axis of the eye. Focusing system 410 focuses primary light beam 185 and secondary light beam 195 onto third beam splitter 420 through spectral isolator 435 and then onto photodetector 440. Spectral isolator 435 is selected so as to prevent the tracking light beam from striking photodetector 440. Preferably, spectral isolator 435 only passes light of the wavelengths of primary light beam 185 and secondary light beam 195. Photodetector 440 is optically focused with the point on the fundus at which primary light beam 185 and secondary light beam 195 strike.

Figure 4:
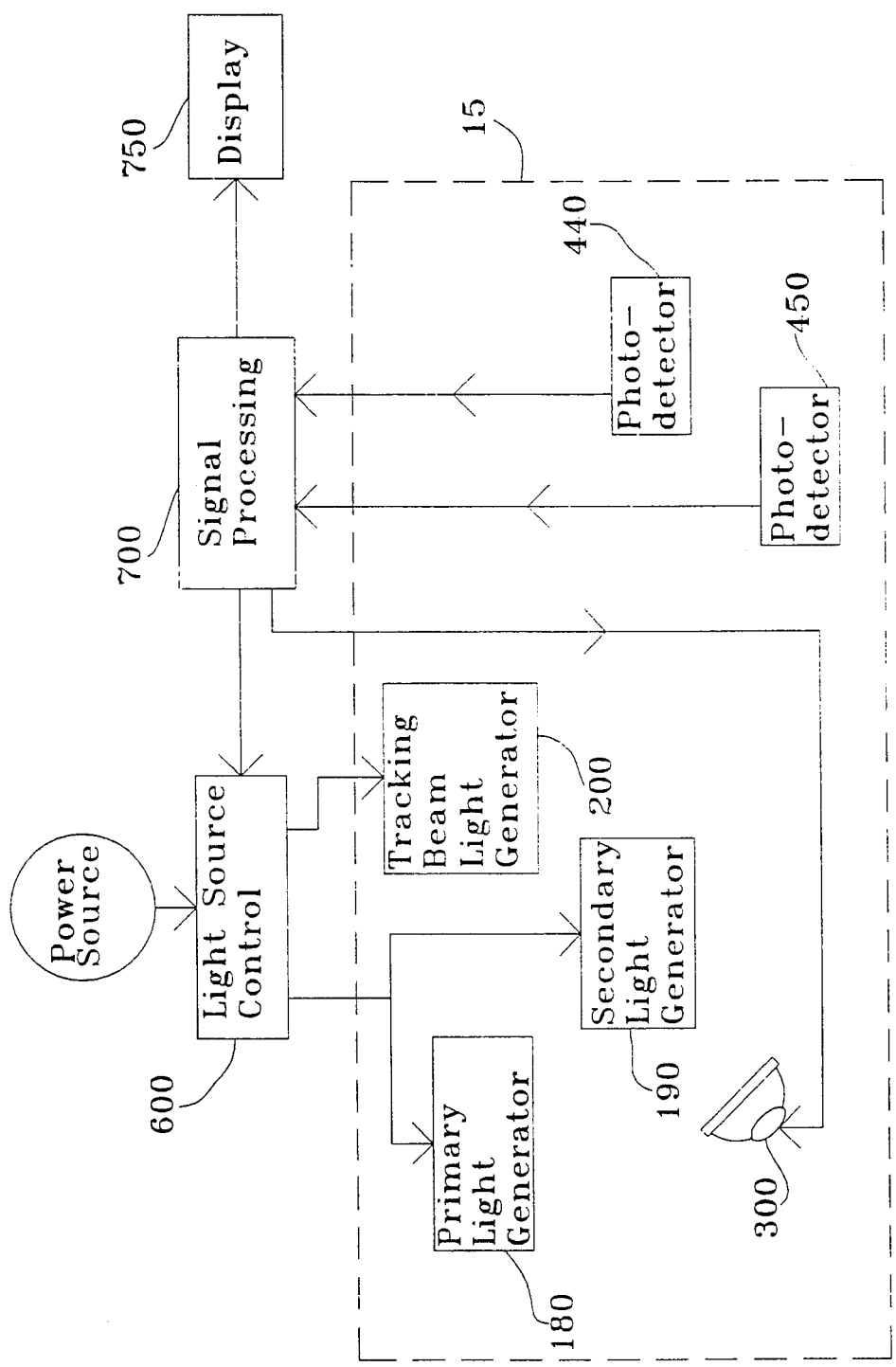
FIG. 4 is a block diagram of the optic disc scanning system of the present invention.

Light source control means 600, shown in FIG. 4 is also critical in preventing the power output of the tracking, primary and secondary light generators from exceeding the safety limit of exposure on the fundus. As mentioned above, light source control 600 also provides the means for emitting light from primary light generator 180 and secondary light generator 190 in a pulsatile, alternating manner. As the light strikes the retinal vessels, the desaturated hemoglobin absorbs and thus reflects light in a quantitatively different way as opposed to saturated hemoglobin. Similarly, the light signal received from the venule is of a different intensity than that of the arteriole. These light signals are detected by photodetector 440 which transmits the electrical signal to signal processing means 700, where noise is filtered from the signals and the signals are amplified. The signals reflected from arterioles are differentiated from the signals reflected from the venules and the difference between arteriole and venule signals is calculated and information concerning the arteriovenous oxygen difference is displayed on display 750. Display 750 can also display separate intensity values for venous and arterial oxygen saturations.

Scanning at time intervals such as every two to three minutes, allows the physician or operator to detect trends in these saturation values, which is useful either at the bedside or prior to and during surgical procedures.

In an alternate embodiment, the present device can be used to detect carboxyhemoglobin content in the blood non-invasively. Narrow bandwidth laser diodes, such as 5 nm width, can be utilized. These diodes avoid overlap in absorption characteristics of carboxyhemoglobin as opposed to deoxyhemoglobin and oxyhemoglobin. A carbon monoxide detector, such as this, employs two judiciously selected wavelengths for primary and secondary light generators 180 and 190, respectively. In this alternate embodiment, primary light generator 180 would emit at $568 \pm 5$ nm, and secondary light generator 190 would emit at a wavelength that is isobestic for hemoglobin and carboxyhemoglobin, such as $548 \pm 5$ nm. This wavelength, 548 nm is a triple isobestic wavelength, i.e. the absorption spectra for deoxyhemoglobin 30, oxyhemoglobin 40 and carboxyhemoglobin 20 each intersect 25 in FIG. 2 at 548 nm. These two highly specific and narrow-band wavelengths allow signal processing means 700 to distinguish between carboxyhemoglobin and oxyhemoglobin or deoxyhemoglobin via reflectance spectrophotometry. Although this method cannot quantitate carboxyhemoglobin content as the in vitro analyzers can, the present invention permits the user to detect its presence, determine an initial baseline reference and then follow the decline in carboxyhemoglobin with time, as treatment for carbon monoxide poisoning is rendered.

Figure 5:
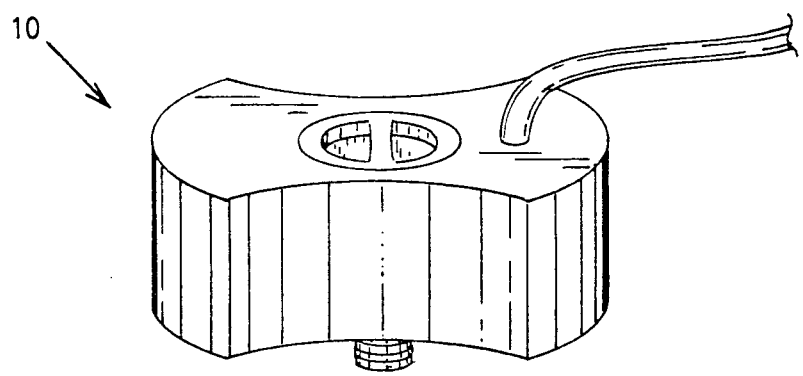
FIG. 5 shows a method for attaching the apparatus of the present invention to the head of the supine subject.
Figure 5:
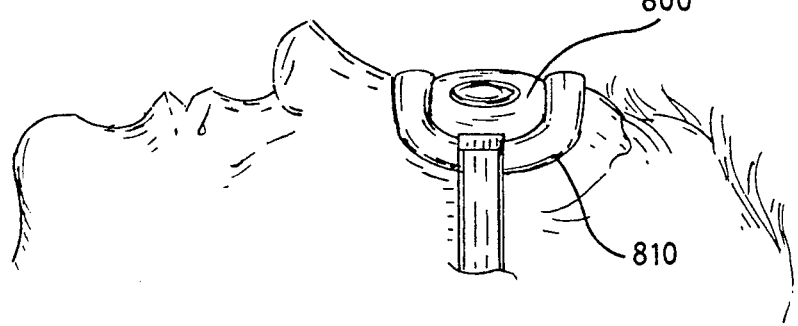

FIG. 5 shows one embodiment for securing the apparatus to a recumbent patients head. Apparatus 10 of the present invention is screwed onto an opaque, periorbital cup 800, which is threaded to receive the device. Once in place, with a snug head band allowing a rubber cushion 810 on the rim of the cup to adhere firmly to the face, ambient light is prevented from entering the eye under examination.

While a preferred embodiment has been shown and described, it will be understood that it is not intended to limit the disclosure, but rather it is intended to cover all modifications and alternate methods falling within the spirit and the scope of the invention as defined in the appended claims or their equivalents.

Having thus described the aforementioned invention, I claim:

1. An ocular fundus scanning system comprising:
   targeting light beam generator means for emitting a targeting light beam having light of at least a first wavelength, said emitted light beam illuminating a portion of a fundus region of an eye including an optic disc, wherein said first wavelength reflects from said optic disc with greater intensity than from fundus tissue surrounding said optic disc;
   targeting light beam focusing means for focusing said targeting light beam as a spot of illumination on said fundus region, said targeting light beam, reflecting from said fundus region thereby forming a reflected targeting beam, and for focusing said reflected targeting light beam;
   targeting light beam detector means for detecting said reflected targeting light beam, said targeting light beam being associated with said targeting light beam focusing means;
   eye scanner means for illuminating a plurality of points within said spot of illumination and for producing a signal proportional to the value of oxygen saturation of oxyhemoglobin in arterioles and venules of said optic disc;
   signal processing means for detecting increased intensity of said reflected targeting light beam as said targeting light beam reflects from said optic disc, said signal processing means activating said eye scanner means when said increased intensity of said reflected targeting beam is detected, analyzing said signals proportional to oxygen saturation of oxyhemoglobin and determining a value of arteriovenous oxygen difference; and
   display means for displaying information concerning said arteriovenous oxygen difference.

2. The ocular fundus scanning system of claim 1 wherein said fundus scanning system further comprises a targeting light beam spectral isolator means for passing light of said first wavelength in cooperation with said targeting light beam generator means.

3. The ocular fundus scanning system of claim 1 wherein said targeting light beam has a wavelength not substantially longer than 589 nm.

4. The ocular fundus scanning system of claim 1 wherein said scanning system further comprises an optic disc scanner housing means for containing said targeting light beam generator means, said targeting light beam focusing means, and said eye scanner means, and light shielding means for blocking out extraneous light in cooperation with said optic disc scanner housing means.

5. The ocular fundus scanning system of claim 1 wherein said eye scanner means comprises:
   primary light beam generator means for generating a primary light beam of a second wavelength, wherein said second wavelength is selected so as to have a low value of absorbance by oxyhemoglobin;
   secondary light beam generator means for generating a secondary light beam of an isobestic wavelength;
   first scanning beam focusing means for focusing said primary light beam and said secondary light beam within said targeting beam spot of illumination;
   means for altering a light path of said primary and secondary light beams, said altering means allowing said beams to inscribe a path on said optic disc;
   second scanning beam focusing means for focusing said primary and secondary light beams reflected from said optic disc;
   scanning beam detector means for detecting said reflected primary and secondary light beams said scanning beam detector means producing signals proportional to oxygen saturation of oxyhemoglobin in said arterioles and venules of said optic disc; and
   light source control means for activating and controlling said targeting light beam and said primary and secondary light beams, said light source control means being associated with and activated by said signal processing means.

6. The ocular fundus scanning system of claim 5 wherein said light source control means simultaneously deactivates said targeting light beam and activates said primary and secondary light beams, said light source control means activating said primary and secondary light beams in a pulsatile, alternating fashion.

7. The ocular fundus scanning system of claim 5 wherein said light path altering means is in association with said first scanning beam focusing means.

8. The ocular fundus scanning system of claim 5 wherein said scanning beam detector means is in association with said second scanning beam focusing means.

9. An ocular fundus scanning system comprising:
targeting light beam generator means for emitting a targeting light beam having light of a first wavelength, said emitted light beam illuminating a portion of a fundus region of an eye, said fundus region including an optic disc, wherein said targeting light beam has a wavelength not substantially longer than 589 nm, said targeting light beam reflecting from said optic disc with greater intensity than from fundus tissue surrounding said optic disc;
first targeting light beam focusing means for focusing said targeting light beam as a spot of illumination on said fundus region, said targeting light beam reflecting from said fundus region thereby forming a reflected targeting beam;
second targeting light beam focusing means for focusing said reflected targeting light beam;
targeting light beam photodetector means for detecting said reflected targeting light beam, said targeting light beam photodetector means being associated with said second targeting light beam focusing means;
primary light beam generator means for generating a primary light beam of a second wavelength, wherein said second wavelength is selected so as to have a low value of absorbance by oxyhemoglobin;
secondary light beam generator means for generating a secondary light beam of an isobestic wavelength;
first scanning beam focusing means for focusing said primary light beam and said secondary light beam within said targeting beam spot of illumination;
galvanometer means for slightly altering a light path of said primary and secondary light beams, said galvanometer means causing said primary and secondary light beams to inscribe a curvilinear path across arterioles and venules of said optic disc, said galvanometer means being associated with said first scanning beam focusing means;
second scanning beam focusing means for focusing said primary and secondary light beams as said primary and secondary light beams reflect from said arterioles and venules of said optic disc;
scanning beam photodetector means for detecting said reflected primary and secondary light beams said scanning beam photodetector means producing signals proportional to oxygen saturation of oxyhemoglobin in said arterioles and venules of said optic disc, said scanning beam photodetector means being associated with said second scanning beam focusing means;
signal processing means for detecting increased intensity of said reflected targeting light beam as said targeting light beam reflects from said optic disc, for analyzing said signals proportional to oxygen saturation of oxyhemoglobin and for determining a value of arteriovenous oxygen difference;
light source control means for simultaneously deactivating said targeting light beam and activating said primary and secondary light beams in a pulsatile alternating fashion said light source control means being associated with said signal processing means, said light source control means being activated by said signal processing means;
display means for displaying said determined value of arteriovenous oxygen difference; and
optic disc scanner housing means for containing said first targeting light beam generator means, said targeting light beam focusing means, said primary and secondary light beam generator means and said first and second scanning beam focusing means, and a light shield means for blocking extraneous light in cooperation with said optic disc scanner housing means.

10. The ocular fundus scanning system of claim 9 wherein said first targeting light beam focusing means also collimates said targeting light beam.

11. The ocular fundus scanning system of claim 9 wherein said first targeting light beam focusing means forces said targeting light beam to form a spot of illumination having a diameter large enough to substantially envelop said optic disc.

12. The ocular fundus scanning system of claim 9 wherein said primary and said secondary light beam to generator means generates said primary and secondary each form a spot of illumination, of said fundus region, having a diameter in a range of approximately 50 to 100 microns.

13. A method of determining arteriovenous oxygen difference which comprises the steps of:
illuminating a fundus region of an eye, said fundus region including an optic disc, with light of a wavelength that is reflected by said optic disc with greater intensity than by tissue surrounding said optic disc;
detecting said greater intensity of said light when said light is reflected by said optic disc;
focusing a primary wavelength of light that has a low value of absorbance by oxyhemoglobin and a substantially isobestic wavelength of light on said optic disc region and illuminating a plurality of points in a curvilinear path on said optic disc region by alternating activation of said primary wavelength of light and said substantially isobestic wavelength of light in a pulsatile fashion, when said greater intensity of said light, reflected by said optic disc, is detected, causing said primary wavelength of light and said substantially isobestic wavelength of light to reflect from vasculature of said optic disc region of said fundus;
detecting said reflected primary and isobestic wavelengths of light, thereby producing signals proportional to values of oxygen saturation of oxyhemoglobin in arterioles and venules of said optic disc; and
calculating said arteriovenous oxygen difference by reflectance spectrophotometry means using said signals proportional to values of oxygen saturation.

14. The ocular fundus scanning system comprising:
targeting light beam generator means for emitting a targeting light beam having light of at least a first wavelength, said targeting light beam generator means illuminating a portion of a fundus region of an eye including an optic disc, wherein said first wavelength reflects from said optic disc with greater intensity than from fundus tissue surrounding said optic disc;

targeting light beam focusing means for focusing said targeting light beam as a spot of illumination on said fundus region, said targeting light beam reflecting from said fundus region thereby forming a reflected targeting beam, and for focusing said reflected targeting light beam;

targeting light beam detector means for detecting said reflected targeting light beam, said targeting light beam detector means being inserted with said targeting light beam focusing means;

primary light beam generator means for generating a primary light beam of a second wavelength, wherein said second wavelength is selected so as to have a low value of absorbance by oxyhemoglobin;

secondary light beam generator means for generating a secondary light beam of an isobestic wavelength;

first scanning beam focusing means for focusing said primary light beam and said secondary light beam within said targeting beam spot of illumination;

means for altering a light path of said primary and secondary light beams, said altering means causing said primary and secondary light beams to inscribe a path across arterioles and venules of said optic disc, said altering means being associated with said first scanning beam focusing means;

second scanning beam focusing means for focusing said primary and secondary light beams as said primary and secondary light beams reflect from said arterioles and venules of said optic disc;

scanning beam detector means for detecting said reflected primary and secondary light beams, said scanning beam detector means producing signals proportional to oxygen saturation of oxyhemoglobin in said arterioles and venules of said optic disc, said scanning beam detector means being associated with said second scanning beam focusing means;

light source control means for activating and controlling said targeting light beam and said primary and secondary light beams, said light source control means simultaneously deactivating said targeting light beam and activating said primary and secondary light beams, said light source control means activating said primary and secondary light beams in a pulsatile, alternating fashion, signal processing means for detecting increased intensity of said reflected targeting light beam as said targeting light beam reflects from said optic disc, for activating said scanning beam detector means when said increased intensity of said reflected targeting beam is detected and for analyzing said signals proportional to oxygen saturation of oxyhemoglobin and for determining a value of arteriovenous oxygen difference, said light source control means being activated by said signal processing means; and display means for displaying information concerning said arteriovenous oxygen difference.

15. The ocular fundus scanning system of claim 14 wherein said light path altering means is associated with said first scanning beam focusing means.

16. The ocular fundus scanning system of claim 14 wherein said scanning beam detector means is associated with said second scanning beam focusing means.

* * * * *